United States Patent [19]

Isshiki et al.

[11] Patent Number: 4,556,519

[45] Date of Patent: Dec. 3, 1985

[54] PROCESS FOR PRODUCING ACETIC ANHYDRIDE

[75] Inventors: Tomiya Isshiki, Tokyo; Yasuhiko Kijima; Yuh Miyauchi, both of Chiba; Takao Kondo, Tokyo, all of Japan

[73] Assignee: Mitsubishi Gas Chemical Company, Inc., Tokyo, Japan

[21] Appl. No.: 568,526

[22] Filed: Jan. 6, 1984

Related U.S. Application Data

[63] Continuation-in-part of Ser. No. 396,478, Jul. 8, 1982.

[30] Foreign Application Priority Data

Jul. 13, 1981 [JP] Japan ................................ 56-108977
Nov. 6, 1981 [JP] Japan ................................ 56-177951

[51] Int. Cl.$^4$ ............................................ C07C 51/56
[52] U.S. Cl. ..................................... 260/549; 560/232
[58] Field of Search ......................... 260/549; 560/232

[56] References Cited

U.S. PATENT DOCUMENTS 4,115,444  9/1978  Rizkalla ............................... 260/549
4,335,059  6/1982  Rizkalla ............................... 260/549
4,353,844 10/1982  Gauthier-Lafaye ................ 260/549

FOREIGN PATENT DOCUMENTS 0055970 12/1980  European Pat. Off. ............ 260/549
0055192 12/1980  European Pat. Off. ............ 260/549

*Primary Examiner*—Paul J. Killos
*Attorney, Agent, or Firm*—Wenderoth, Lind & Ponack

[57] ABSTRACT

A process for producing acetic anhydride which comprises reacting methyl acetate or dimethyl ether with carbon monoxide in the presence of a catalyst comprising (a) nickel or a nickel compound and (b) at least one halide selected from the group consisting of bromides, iodides and mixtures thereof, and together with a specific co-catalyst which is disclosed. According to this invention acetic anhydride is produced by using highly active non-expensive catalyst and co-catalyst.

24 Claims, No Drawings

PROCESS FOR PRODUCING ACETIC ANHYDRIDE

CROSS REFERENCE TO RELATED APPLICATION

This is a continuation-in-part of application Ser. No. 396,478, filed July 8, 1982.

BACKGROUND OF THE INVENTION

This invention relates to a process for producing acetic anhydride which comprises reacting methyl acetate or dimethyl ether with carbon monoxide in the presence of a catalyst and a co-catalyst.

In the prior art, the known catalysts for producing carboxylic anhydrides from carboxylic esters or ethers and carbon monoxide include the following:
(i) a catalyst comprising a noble metal belonging to Group VIII of the Periodic Table, such as rhodium, a halide and a third component as disclosed in Japanese Patent Publication (Kokoku) No. 3926/1977; Japanese Patent Publication (Kokai) No. 65709/1976 and Japanese Patent Publication (Kokai) No. 115403/1976, Japanese Patent Publication (Kokai) No. 57733/1981 and
(ii) a catalyst comprising nickel or cobalt, a halide and a third component as disclosed in Japanese Patent Publication (Kokai) Nos. 59214/1979, 78814/1977 and 78815/1977 assigned to the assignee of this application, U.S. Pat. Nos. 4,002,677, 4,002,678 and 2,729,651.

However, the catalyst (i) contains expensive rhodium as shown in Hydrocarbon Processing 54, June 83 (1975).

In case of producing carboxylic anhydrides from carboxylic esters or ethers and carbon monoxide by using a rhodium catalyst, a rhodium complex has to be prevented from being reduced to metallic rhodium under a reducing atmosphere as disclosed in Chemistry and Industry 29 (5) page 376 (1975) or the rhodium component has to be prevented from being scattered from the reaction system during the operation of separating the product as disclosed in Japanese Patent Publication (Kokai) No. 90204/1978.

In Japanese Patent Publication (Kokai) No. 59214/1979 assigned to the assignee of this invention, a nickel catalyst has been proposed in place of the noble metal catalyst. However, when using the catalyst (ii) as disclosed in Japanese Patent Publication (Kokai) No. 59214/1979 and U.S. Pat. No. 2,729,651 the reaction rate is low, and the reaction conditions are severe.

SUMMARY OF THE INVENTION

The present inventors carried out research to increase the rate of reaction between methyl acetate or dimethyl ether and carbon monoxide and to use the reaction catalyst (ii) under milder reaction conditions. As a result we have found a process for producing acetic anhydride from methyl acetate or dimethyl ether and carbon monoxide in the presence of a catalyst comprising nickel or a nickel compound and a halide, and a co-catalyst comprising one or more metals belonging to Group IVB of the Periodic Table or compounds of the metals, one or more materials selected from the group consisting of metals belonging to Groups IA and IIA of the Periodic Table, compounds of the metals and mixtures thereof, and optionally one or more metals belonging to Group IVA of the Periodic Table or compounds of the metals.

This invention relates to a process for producing acetic anhydride which comprises reacting methyl acetate or dimethyl ether with carbon monoxide in the presence of a catalyst and a co-catalyst, said catalyst comprising (a) nickel or a nickel compound and (b) a halide or halides selected from bromides, iodides or mixtures thereof; and said co-catalyst comprising a Group IVB metal component, a Group IA and/or Group IIA metal component, and optionally a Group IVA metal component, said Group IVB metal component being one or more materials selected from the group consisting of metals belonging to Group IVB of the Periodic Table, compounds of the metals and mixtures thereof, said Group IA metal component being one or more materials selected from the group consisting of metals belonging to Group IA of the Periodic Table, compounds of the metals and mixtures thereof, said Group IIA metal component being one or more materials selected from the group consisting of metals belonging to Group IIA of the Periodic Table, compounds of the metals and mixtures thereof, and said Group IVA metal component being one or more materials selected from the group consisting of metals belonging to Group IVA of the Periodic Table, compounds of the metals and mixtures thereof.

DETAILED DESCRIPTION OF THE INVENTION

By the "Periodic Table" given in the specification and the claims is meant the Periodic Table in the "Shin Jikken Kagaku Kohza" vol. 12, 1976 pages 4–5 published by the Japan Chemical Association.

In a certain catalyst for the production of acetic anhydride in the prior art, it has been required to use an organic nitrogen group compound as a catalyst component in order to increase the catalytic activity of the catalyst and stabilize the catalyst. For example, the method disclosed in Japanese Patent Publication (Kokai) No. 57733/1981 described hereinbefore requires the presence of as much as 20% of an organic nitrogen group compound as a ligand in the reaction system in addition to the use of an expensive rhodium catalyst. Such a nitrogen group compound as the ligand used in a large amount is highly likely to precipitate from the reaction mixture under separation conditions of the product since the compound is, in general, a solid at ordinary temperature. As a result, the recycling of the catalyst and cocatalyst that is necessary in continuous operation is very difficult, if not impossible. Furthermore, the organic nitrogen group compound is labile, changing to other undesired compounds (see, J. Am. Chem. Soc. Vol., 77, 3883 (1955) and ibid., Vol. 78, 3493 (1956), for example), and thus its activity is reduced. Also, to separate the by-products formed from the reaction mixture requires much energy.

According to this invention, it becomes possible to eliminate the use of such an organic nitrogen group compound and, surprisingly, raising rather than lowering solubility of the catalyst system. Also, it becomes possible to markedly prolong the life of the catalyst and achieve easier separation of the object product from the reaction mixture leading to the saving of energy, because the catalyst system of the invention does not include any catalyst components which are easily decomposable under reaction conditions, and thus makes it to eliminate the formation of by-products derived from the catalyst components.

Nickel or nickel compounds (sometimes hereinunder referred to as the nickel component) constituting the catalyst of this invention include organic or inorganic nickel compounds or metallic nickel. Examples of nickel and nickel compounds include nickel powder, nickel acetate, nickel iodide, nickel acetylacetonate, nickel tetracarbonyl and nickel dicarbonyl.

Halides employed together with the nickel component include bromides, iodides or mixtures thereof. Examples of the halides include alkyl halide, such as methyl iodide, acid halogenides, such as acetyl iodide, or hydrogen halides, such as hydrogen iodide, or mixtures thereof. The halide may be added to a reaction medium as it is. Materials which can convert to an alkyl halide, an acid halogenide or a hydrogen halide can be used as a halide constituting the catalyst of this invention. Examples of the materials which convert to an alkyl halide, an acid halogenide or a hydrogen halide by reacting with components in the reaction medium include inorganic halides, such as alkali metal halides, such as lithium, sodium or potassium halides; alkaline earth metal halides, such as magnesium or calcium halides; metal halides such as aluminum, zinc, copper, lanthanum, or cerium halides; or bromine or iodine. When halides of metals belonging to Groups IA, IIA, IVA or IVB of the Periodic Table are used as a halide constituting the catalyst of this invention, they also serve as a component constituting the co-catalyst of this invention. Of the halides, methyl halides, such as methyl iodide, are preferable, because the use of these compounds facilitates the selection of a corrosion-resistant reactor; separation of the reaction product from the reaction mixtures, and purification of the reaction product.

Though the reaction of methyl acetate or dimethyl ether with carbon monoxide proceeds in the presence of only the catalyst employed in this invention which comprises (a) the nickel component and (b) the halide, the catalyst has only poor activity in the reaction. When the reaction is carried out in the presence of the catalyst together with a co-catalyst comprising one or more materials selected from metals belonging to Group IVB of the Periodic Table, compounds of the metals and mixtures thereof, and one or more materials selected from the group consisting of metals belonging to Groups IA and IIA of the Periodic Table, compounds of the metals and mixtures thereof, the reaction proceeds speedily. Moreover, when at least one material selected from metals belonging to Group IVA of the Periodic Table, compounds of the metals and mixtures thereof, which is an optional component of the present catalyst system, is used in combination with the catalyst and co-catalyst above described, it can result in an increase in the activity of the catalyst, compared with the case of not using the Group IVA metal or metal compound.

Preferable metals of Group IVB and compounds of the metals include silicon, germanium and tin, and compounds of the metals. Tin and tin compounds are most preferable.

Preferable metals of Group IA and compounds of the metals include lithium, sodium, potassium, rubidium and cesium, and compounds of the metals. Lithium, rubidium and cesium, and compounds of these metals are more preferable; and lithium and its compounds are most preferable.

Preferable metals of Group IIA and compounds of the metals include beryllium, magnesium, calcium, strontium and barium and compounds of the metals. Magnesium, calcium, strontium and barium and compounds of the metals are more preferable; and calcium and strontium and compounds of these metals are most preferable.

Preferable metals of Group IVA and compounds of the metals include titanium, zirconium and hafnium and compounds of the metals. Zirconium and hafnium and compounds of the metals are more preferable; and zirconium and its compounds are most preferable.

By combining the nickel catalyst with the metal of Group IVB or the compound thereof and at least one material selected from metals of Groups IA and IIA and compounds thereof, and optionally the metal of group IVA or the compound thereof, a remarkable increase in the catalytic activity, i.e. the formation rate of acetic anhydride (in grams) per gram of elemental nickel per gram of elemental halogen per hour is obtained.

The metals belonging to Groups IVB, IA, IIA and optionally IVA of the Periodic Table may be used in the form of element or in the form of compounds. For example, they can be used as metal itself or Raney metals, or finely divided particles of the metals, or as metal compounds, such as carbonates, oxides, hydroxides, nitrates, sulfates, phosphates, halides, cyanides, thiocyanides, sulfonates, $C_1$-$C_5$ lower alkoxides, such as methoxides and ethoxides, phenoxide, metal carboxylates derived from $C_1$-$C_{20}$ alkanoic acids, oxyhalides, hydrides, nitrites, sulfites, phosphites, acetylacetonates and sulfides of metals, or metal compounds coordinated with ammonia, cyanide, amines or amino acids, or organic metal compounds having phenyl group or alkyl group.

Metals of Groups IVB, IA, IIA and IVA and compounds of the metals include, for example, $H_2SiO_3$, $H_4SiO_4$, $SiHBr_3$, $SiHCl_3$, $SiHF_3$, $SiHI_3$, $Si$, $Si_2Br_6$, $SiBr_4$, $SiBrH_3$, $SiBrCl_3$, $SiBr_2Cl_2$, $SiBr_3Cl$, $Si_2Cl_6$, $SiCl_4$, $SiClH_3$, $SiF_4$, $SiH_4$, $Si_2H_6$, $Si_2H_8$, $Si_4H_{10}$, $SiI_2$, $Si_2I_6$, $SiI_4$, $SiICl_3$, $SiO_2.XH_2O$, $SiO_2$, $Si_2OCl_6$, $SiS$, $SiS_2$, $Ge$, $GeBr_4$, $GeCl_2$, $GeCl_4$, $GeHCl_3$, $GeF_4.3H_2O$, $GeH_4$, $GeI_4$, $GeO$, $GeO_2$, $GeOCl_2$, $GeS$, $GeS_2$, $Sn$, $SnBr_4$, $SnCl_4$, $SnF_4$, $SnI_4$, $SnO_2$, $SnOCl_2$, $2SnO_2.P_2O_5.10H_2O$, $SnP$, $Sn(SO_4)_2.2H_2O$, $SnS_2$, $SnBr_2$, $SnCl_2$, $SnF_2$, $Sn(OH)_2$, $SnI_2$, $SnC_2O_4$, $SnO$, $SnO.SnCl_2.3H_2O$, $SnSO_4$, $SnS$, $Sn(C_6H_5)_4$, $Sn(CH_3)_4$, $Sn(CH_3)_2$, $Sn(C_2H_5)_4$, $(C_3H_7)_2SnH_2$, $(CH_2)_2SnI_2$, $Sn(C_2H_5)_2$, $(C_4H_6)_2SnCl_2$, $(C_2H_5)_2SnI_2$, $(CH_3)_3SnCl$, $(C_4H_9)_2SnH_2$, $(C_3H_7)_2SnI_2$, $(CH_3)_3(CH_2I)Sn$, $(C_4H_9)_3SnCl$, $(C_4H_9)_2SnI_2$, $(C_2H_5)_3SnCl$, $(C_4H_9)_3SnH$, $(C_2H_5)_3SnH$, $(C_6H_5CH_2)_3SnCl$, $Sn(C_2H_3O_2)_2$, $SnHPO_4$, $Sn(C_2H_3O_2)_4$, $PtH(SnCl_3)$ $(CO).(Pph_3)_2$, $Li$, $LiC_2.H_3O_2.2H_2O$, $LiAlO_2$, $LiNH_2$, $LiBO_2$, $Li_2B_4O_7.5H_2O$, $LiBr$, $LiBr.2H_2O$, $Li_2CO_3$, $LiHCO_3$, $LiClO_3$, $LiClO_3.0.5H_2O$, $LiCl$, $Li_3C_6H_5O_7.4H_2O$, $Li_2S_2O_6.2H_2O$, $LiF$, $Li_2[SiF_6].2H_2O$, $LiHCO_2.H_2O$, $LiH$, $LiOH$, $LiOH.H_2O$, $LiI$, $LiI.3H_2O$, $LiNO_3$, $LiNO_3.3H_2O$, $LiNO_2.H_2O$, $Li_2C_2O_4$, $LiHC_2O_4.H_2O$, $Ki_2O$, $LiClO_4$, $LiClO_4.3H_2O$, $LiMnO_4$, $LiH_2PO_4$, $Li_3PO_4$, $Li_3PO_4.12H_2O$, $Li_2SiO_3$, $Li_4SiO_4$, $Li_2SO_4$, $Li_2SO_4.H_2O$, $LiHSO_4$, $Li_2S$, $Li_2SO_3$, $Rb$, $RbBrO_3$, $RbBr$, $RbBr_3$, $Rb_2CO_2$, $RbHCO_3$, $RbClO_3$, $RbCl$, $RbF$, $RbH$, $RbOH$, $RbIO_3$, $RbI$, $RbI_3$, $RbNO_3$, $Rb_2O$, $Rb_2O_2$, $Rb_2O_3$, $Rb_2O_4$, $RbClO_4$, $RbIO_4$, $RbMnO_4$, $Rb_2SeO_4$, $Rb_2SO_4$, $Rb_2S$, $Rb_2S.4H_2O$, $Rb_2S_5$, $Rb(C_2H_3O_2)$, $Cs$, $CsBrO_3$, $CsBr$, $CsBr_3$, $Cs_2CO_2$, $CsHCO_3$, $CsCl$, $CsCN$, $CsF$, $CsH$, $CsOH$, $CsIO_3$, $CsI$, $CsI_3$, $CsNO_3$, $CsNO_2$, $Cs_2O$, $Cs_2O_2$, $Cs_2O_3$, $Cs_2O_4$, $CsClO_4$, $CsIO_4$, $CsMnO_4$, $Cs_3SiW_{12}O_{42}$, $Cs_2SO_4$, $CsHSO_4$, $Cs_2.4H_2O$, $Cs_2S_2$, $Cs_2S_2.H_2O$, $Cs_2S_3$, $Cs_2S_5$, $CsHC_4H_4O_6$, $Cs(C_2H_3O_2)$, Mg, $Mg(C_2H_3O_2)_2$, $Mg(C_2H_2O_2)_2.4H_2O$, $MgO.Al_2O_3$, $MgCl_2.NH_4Cl.6H_2O$, $MgNH_4PO_4.6H_2O$, $MgSO_4.(NH_4)_2SO_4.6H_2O$, $Mg(BO_2)_2.8H_2O$, $Mg(BrO_3)_2.6H_2O$, $MgBr_2$, $MgBr_2.6H_2O$, $MgCO_3$, $MgCO_3.3H_2O$, $3MgCO_3.Mg(OH)_2.3H_2O$, $Mg(ClO_3)_2.6H_2O$, $MgCl_2$, $MgCl_2.6H_2O$, $MgF_2$, $Mg[SiF_6].6H_2O$, $Mg(OH)_2$, $Mg(H_2PO_2)_2.6H_2O$, $Mg(IO_2)_2.4H_2O$, $MgI_2$, $Mg(NO_3)_2.6H_2O$, $Mg_3N_2$, $MgC_2O_4.2H_2O$, MgO, $Mg(ClO_4)_2.6H_2O$, $Mg(MnO_4)_2.6H_2O$, $Mg_3(PO_4)_2.4H_2O$, $Mg_3(PO_4)_2.8H_2O$, $MgHPO_4.3H_2O$, $MgHPO_4.7H_2O$, $Mg_2P_2O_7$, $Mg_2P_2O_7.3H_2O$, $MgHPO_3.3H_2O$, $MgCl_2.KCl.6H_2O$, $MgSO_4.K_2SO_4.6H_2O$, $MgCl_2.NaCl.H_2O$, $MgSO_4$, $MgSO_4.7H_2O$, MgS, $MgSO_3.6H_2O$, $Mg(C_4H_4O_6).5H_2O$, $MgS_2O_3.6H_2O$, Ca, $Ca(C_2H_3O_2)_2.H_2O$, $Ca(AlO_2)_2$, $CaO.Al_2O_3.2SiO_2$, $CaNH_4AsO_4.6H_2O$, $CaNH_4PO_4.7H_2O$, $Ca_3(AsO_4)_2$, $Ca(BO_2)_2.2H_2O$, $CaB_6$, $Ca(BrO_2)_2.H_2O$, $CaBr_2$, $CaBr_2.6H_2O$, $CaC_2$, $CaCO_3$, $Ca(ClO_3)_2.2H_2O$, $CaCl_2$, $CaCl_2.H_2O$, $CaCl_2.6H_2O$, $Ca_3(C_6H_5O_7)_2.4H_2O$, $Ca(CN)_2$, $CaCN_2$, $CaS_2O_6.4H_2O$, $CaF_2$, $Ca[SiF_6]$, $Ca[SiF_5].2H_2O$, $Ca(HCO_2)_2$, $CaH_2$, $Ca(SH)_2.6H_2O$, $Ca(OH)_2$, $Ca(ClO)_2.4H_2O$, $Ca(IO_3)_2$, $CaI_2$, $CaI_2.6H_2O$, $Ca(C_3H_5O_3)_2.5H_2O$, $CaO.MgO.2CO_2$, $CaO.MgO.2SiO_2$, $CaMoO_4$, $Ca(NO_3)_2$, $Ca(NO_3)_2.4H_2O$, $Ca_3N_2$, $Ca(NO_2)_2.H_2O$, $CaC_2O_4$, CaO, $Ca(MnO_4)_2.4H_2O$, $CaO_2.8H_2O$, $CaHPO_4.2H_2O$, $Ca_2P_2O_6.2H_2O$, $Ca(PO_3)_2$, $Ca(H_2PO_4)_2.H_2O$, $Ca_2P_2O_7$, $Ca_2P_2O_7.5H_2O$, $Ca_3(PO_4)_2.2CaHPO_3.3H_2O$, $Ca(H_2PO_2)_2$, $CaK_2(SO_4)_2.H_2O$, $CaSiO_2$, $CaSi_2$, $CaSO_4.2Na_2SO_4.2H_2O$, $CaSO_4$, $CaSO_4.2H_2O$, $CaSO_4.0.5H_2O$, CaS, $CaSO_2.2H_2O$, $CaC_4H_4O_6.4H_2O$, $CaCS_3$, $Ca(SCN)_2.3H_2O$, $CaS_2O_3.6H_2O$, $CaWO_4$, Sr, $Sr(C_2H_2O_2)_2$, $SrB_4O_7.4H_2O$, $Sr(BrO_3)_2.H_2O$, $SrBr_2$, $SrBr_2.6H_2O$, $SrCO_3$, $Sr(ClO_3)_2$, $Sr(ClO_3)_2.8H_2O$, $SrCl_2$, $Sr(CN)_2.4H_2O$, $SrS_2O_6.4H_2O$, $SrF_2$, $Sr[SiF_6].2H_2O$, $Sr(HCO_2)_2$, $Sr(HCO_2)_2.2H_2O$, $Sr(SH)_2$, $Sr(OH)_2$, $Sr(OH)_2.8H_2O$, $Sr(IO_3)_2$, $SrI_2$, $SrI_2.6H_2O$, $Sr(NO_3)_2$, $Sr(NO_3)_2.4H_2O$, $Sr(NO_2)_2$, $Sr(NO_2)_2.H_2O$, $SrC_2O_4.H_2O$, SrO, $SrO_2$, $SrO_2.8H_2O$, $Sr(MnO_4)_2.3H_2O$, $SrHPO_4$, $SrSiO_3$, $SrSO_4$, $Sr(HSO_4)_2$, SrS, $SrS_4.6H_2O$, $Sr(CNS)_2.3H_2O$, $SrS_2O_3.5H_2O$, Ba, $Ba(C_2H_3O_2)_2$, $Ba(C_2H_3O_2)_2.H_2O$, $Ba(NH_3)_2$, $Ba_3(AsO_4)_2$, $BaHAsO_4.H_2O$, $Ba(Ns)_2$, $Ba(Ns)_2.H_2O$, $Ba(BrO_2)_2.H_2O$, $BaBr_2$, $BaBr_2.2H_2O$, $Ba[PtBr_6].10H_2O$, $BaC_2$, $BaCO_2$, $Ba(ClO_3)_2$, $Ba(ClO_2)_2.H_2O$, $BaCl_2$, $BaCl_2.2H_2O$, $Ba(CN)_2$, $BaS_2O_6.2H_2O$, $BaF_2$, $Ba[SiF_6]$, $Ba(HCO_2)_2$, $BaH_2$, $Ba(SH)_2.4H_2O$, $Ba(OH)_2$, $Ba(OH)_2.8H_2O$, $Ba(ClO)_2$, $BaPO_3$, $Ba(H_2PO_2)_2.H_2O$, $Ba(IO_3)_2$, $Ba(IO_3)_2.H_2O$, $BaI_2.2H_2O$, $BaI_2.6H_2O$, $BaMnO_4$, $BaMoO_4$, $Ba(NO_3)_2$, $Ba(NO_2)_2$, $Ba(NO_2)_2.H_2O$, $BaC_2O_4$, BaO, $Ba(ClO_4)_2$, $Ba(ClO_4)_2.3H_2O$, $Ba(MnO_4)_2$, $BaO_2$, $BaO_2.8H_2O$, $BaS_2O_8.4H_2O$, $BaHPO_4$, $Ba(H_2PO_4)_2$, $Ba_2P_2O_7$, $Ba_2(PO_4)_2$, $BaSiO_3$, $BaSiO_3.6H_2O$, $BaSO_4$, BaS, $BaS_4.2H_2O$, $BaS_3$, $BaSO_3$, $Ba(CNS)_2.2H_2O$, $BaS_2O_3.H_2O$, $TiF_4$, $TiCl_4$, $TiBr_4$, $TiI_4$, $5TiO_2.N_2O_5.6H_2O$, $Ti_2(C_2O_4)_2.10H_2O$, $TiO_2$, $Ti_2O_3$, $Ti_2(SO_4)_3$, $ZrF_4$, $ZrCl_4$, $ZrBr$, $ZrI_4$, $Zr(OH)_4$, $Zr(NO_3)_4.5H_2O$, $Zr(C_2O_4)_2.2Zr(OH)_4$, $ZrO_2$, $ZrOBR_2.8H_2O$, Zr, $ZrOCl_2.8H_2O$, $ZrI(OH)_3.3H_2O$, $ZrOI_2.8H_2O$, $Zr(SO_4)_2.4H_2O$, Hf, $HfO_2$, and $HfCl_4$.

Since a halide, such as bromide or an iodide is used as one component of the catalyst and the object product is an organic acid anhydride, it is preferable that the co-catalyst metal is used in the form of a halide, such as bromide or iodide, or an organic acid salt, such as acetate.

Though the catalyst system needs no other component other than the essential and optional components described hereinbefore, if desired, any other metal materials capable of offering any good effect on the reaction may be used in addition to these essential and optional components. Examples of such materials include one or more materials selected from the group consisting of metals belonging to Groups IIIA, VIA and IIIB of the Periodic Table, compounds of the metals and mixtures thereof.

The amount of the nickel component employed as one component of the catalyst in this invention may be in the range of $1 \times 10^{-6}$ g-atom–5 g-atom, preferably $1 \times 10^{-4}$ g-atom–2 g-atom, more preferably $1 \times 10^{-3}$ g-atom–1 g-atom and most preferably $5 \times 10^{-3}$ g-atom–0.5 g-atom per 1 liter of a reaction solution in terms of metal.

The amount of the halide employed as one component of the catalyst may be in the range of from $10^{-3}$ mol–15 mol, preferably $10^{-2}$ mol–8 mol and more preferably $10^{-1}$ mol–4 mol and most preferably $2 \times 10^{-1}$ mol–2.5 mol per 1 liter of a reaction solution in terms of halogen atom.

The amount of each of the Group IVB, Group IA, Group IIA and Group IVA metal components constituting the co-catalyst of this invention may be in the range of 0.01 g-atom–100 g-atom [Ni:Group IVB metal:Group IA and/or IIA metal:Group IVA metal (optional) = 1:(0.01-100):(0.01-100):(0.01-100) g-atom ratio], preferably 0.03 g-atom–30 g-atom [Ni:Group IVB metal:Group IA and/or IIA metal:Group IVA metal (optional) = 1:(0.03-30):(0.03-30):(0.03-30) g-atom ratio] and most preferably 0.1 g-atom–20 g-atom [Ni:Group IVB metal:Group IA and/or IIA metal:Group IVA metal (optional) = 1:(0.1-20):(0.1-20):(0.1-20) g-atom ratio] per 1 g-atom of nickel in terms of elementary metal. However, in general, the amount of each of the metal component constituting the co-catalyst may be in the range of $10^{-5}$ g-atom–30 g-atom, preferably $1 \times 10^{-4}$ g-atom–1 g-atom and most preferably $1 \times 10^{-3}$ g-atom–0.5 g-atom per 1 liter of a reaction solution in terms of elementary metal. In general, the amount of the Group IA or Groups IIA component employed may be in the range of $1 \times 10^{-3}$ g-atom–$1 \times 10^3$ g-atom, preferably $1 \times 10^{-2}$ g-atom–$1 \times 10^2$ g-atom and most preferably 0.1 g-atom–50 g-atom per g-atom of the metal of Group IVB or compound of the metal in terms of metal, or of the metals of Group IVA and IVB or compounds of the metals in terms of metal when the co-catalyst further contains a Group IVA metal component.

In practicing this invention, the reaction temperature is not critical. In general, the reaction temperature may be in the range of 20° C.–350° C., preferably 80° C.–300° C. and most preferably 100° C.–250° C.

The reaction pressure is kept high enough to keep the raw material(s), the solvent and the product in a liquid phase and to maintain appropriately partial pressure of carbon monoxide. The partial pressure of carbon monoxide may be in the range of 0.5 atm.–300 atm., preferably 1 atm.–200 atm., and most preferably 3 atm.–150 atm.

Dimethyl ether and methyl acetate which are used as starting materials in this invention may be prepared by known methods. For example, dimethyl ether may be produced from CO and $H_2$ directly or by dehydration-dimerization reaction of methanol.

Methyl acetate may be produced by esterification of methanol and acetic acid. In this reaction acetic acid may be produced by reacting methanol with carbon monoxide (refer to Patent Publication (Kokai) Nos. 59211/1979, 63002/1979 and 66614/1979). Methyl acetate formed together with PVA in a process for converting polyvinyl acetate to PVA may be used as a starting material in the present invention. Methyl acetate produced by reaction methanol with synthesis gas as exemplified in Japanese Patent Publication (Kokoku) No. 2525/1973, and Japanese Patent Publications (Kokai) Nos. 149213/1976, 136110/1977 and 136111/1977 may be used in the present invention. Methyl acetate produced in the above methods may contain methanol, dimethyl ether, acetic acid, acetaldehyde, dimethyl acetal and halides, such as methyl iodide as impurities. However, incorporation of these compounds in methyl acetate is permitted as long as an overall balance is obtained.

When methyl acetate containing methanol or a small amount of water is used as the starting material, acetic acid may be simultaneously produced together with acetic anhydride. This simultaneous production of the two compounds may be advantageous for a certain purpose.

Dimethyl ether is considered to be a precursor of methyl acetate in the carbonylation reaction. Therefore, when the term "methyl acetate" is used as a starting material for preparing acetic anhydride, dimethyl ether should be included in the methyl acetate.

The carbon monoxide employed as a raw material gas does not need to be highly pure and may contain hydrogen, carbon dioxide, methane, nitrogen, rare gases and water. Hydrogen does not interfere the carbonylation reaction but, rather, stabilizes the catalyst.

When metals of Group VIII of the Periodic Table excluding nickel, such as rhodium or palladium or compounds of the metals are used as catalyst, by-products, such as ethylidene diacetate and acetaldehyde are formed in the presence of carbon monoxide and hydrogen, as exemplified in Japanese Patent Publication (Kokai) No. 115409/1976. However, even if carbon monoxide and hydrogen are present in the reaction system, such by-products are almost unformed in the presence of a nickel component as a metal component constituting the catalyst. Therefore, the nickel component exhibits different properties from those of a rhodium or palladium system. An extremely low concentration of carbon monoxide in the reaction system is not desirable, because the reaction pressure must be raised when such a gas is used.

In general, water is incorporated into the reaction system, because commercially available raw material gas and methyl acetate or dimethyl ether contain a small amount of water. Raw material gas and methyl acetate or dimethyl ether containing water of such low concentration are permitted in this invention. The presence of water of more than 10% by weight on the basis of weight of a reaction solution is not preferable in this process, because such a large amount of water causes the starting materials and the products to decompose.

In general, a water content of less than 7% by weight is preferable, and water content less than 5% by weight is more preferable. When the raw materials contain a large amount of water, they should be dried before introducing them into the reaction system.

Since methyl acetate or dimethyl ether (as a starting material) and/or acetic anhydride (object product) serves as a solvent for the reaction of this invention, another solvent may not be used. Any organic solvent or diluent compatible with the starting material and the object product under the reaction conditions may be used.

Preferable solvents are materials capable of participating in the reaction as a component constituting the catalyst, a raw material, an intermediate, or a product. Such solvents are methyl iodide, methyl acetate, acetic anhydride and acetic acid. Of these solvents, acetic acid is preferable since it has a tendency to stabilize the catalyst and accelerate the reaction, and it is a compound analogous to the product, i.e. acetic anhydride.

Solvents or diluents other than those which participate in the reaction can be used in this invention. Examples of such solvents include organic acid esters such as ethylene glycol diacetate, propylene glycol diacetate, dimethyl adipate, methyl benzoate, phenyl acetate and dimethyl phthalate; hydrocarbons, such as dodecane, hexadecane, benzene, naphthalene, and biphenyl; and inorganic acid esters, such as triphenyl phosphate, tricresyl phosphate, dibutylphenyl phosphate, tetramethyl orthosilicate and tetrabutyl silicate.

The present process may be carried out by batch, semi-continuous or continuous method. When the invention is carried out as a continuous process, acetic anhydride, unreacted methyl acetate or dimethyl ether, the halides and the metal catalyst components may be recovered by a separating operation, such as distillation from reaction mixture withdrawn from carbonylation reaction. The halides and metal catalytic components which have been recovered may be recirculated into the reaction system.

The separating zone comprises one or more distilling units, for example, the flash distillation and/or purifying columns. Acetic anhydride can be withdrawn in a gaseous state by distillation in the carbonylation reaction zone from the reaction mixture. The gaseous mixture contains non-condensable gas, such as carbon monoxide and hydrogen, (it is contained only in a certain case) and acetic anhydride, unreacted methyl acetate or dimethyl ether, halides and nickel compounds (it is contained only in a certain case). In general, the co-catalyst is non-volatile, so it remains in the reaction zone together with most of the nickel component. The gaseous mixture may be cooled and condensed. The non-condensable components may be recycled into the carbonylation reaction zone and fresh carbon monoxide and hydrogen (if necessary) may be introduced into the reaction zone to increase the pressure of carbonylation reaction zone to a desired extent.

Components condensed from the reaction mixture may be subjected to distillation to separate each components. The resulting unreacted methyl acetate or dimethyl ether and halides may be recycled into the reaction zone.

Part of the reaction mixture gas may be purged from the reaction system to prevent accumulation of impurities, such as nitrogen introduced into the system with carbon monoxide and hydrogen and by-products, such as methane formed in the reaction system.

The present invention is characterized by production of acetic anhydride by reaction of methyl acetate or dimethyl ether and carbon monoxide by using highly active non-expensive catalyst and co-catalyst, so the present invention is preferable from an industrial point of view.

The following examples are given as illustrative embodiment of the invention and should not be construed as limiting its scope.

All parts and percents are on weight, unless otherwise specified. In examples, Ac represents an acetyl group and Me represents a methyl group.

The term "formation rate of acetic anhydride" as used in the Examples means the amount of acetic anhydride yielded per gram of elemental nickel per gram of elemental iodine per hour as represented by the equation ide was carried out at 180° C. for one hour while maintaining the pressure at 80 atm. by continuously feeding carbon monoxide into the autoclave. After completing the reaction, analysis showed that the yield of acetic anhydride was 73.2% on the basis of methyl acetate.

EXAMPLES 2-12

Procedures similar to those of Example 1 were followed in which the feeding materials and reaction conditions shown in Table 1 were used.

The results obtained are given in Table 1 together with those of Example 1.

TABLE 1

| Ex. No. | AcOMe (g) | Solvent (g) | Nickel Component (g) | Halide (g) | Co-catalyst I (g) | Co-catalyst II (g) | Co-catalyst III (g) |
|---|---|---|---|---|---|---|---|
| 1 | 29.6 | AcOH 24.0 | Ni powder 0.208 | $CH_3I$ 13.9 | $Sn(OAc)_2$ 1.67 | LiOAc 2.64 | |
| 2 | 29.6 | AcOH 24.0 | Ni powder 0.208 | $CH_3I$ 13.9 | $SnI_4$ 2.2 | LiOAc 2.64 | |
| 3 | 29.6 | AcOH 24.0 | $Ni(OAc)_2$ 0.625 | $CH_3I$ 6.0 | $Sn(OAc)_2$ 0.84 | LiI 5.36 | |
| 4 | 29.6 | $Ac_2O$ 24.0 | $NiI_2$ 1.11 | $CH_3I$ 13.9 | $Sn(OAc)_2$ 1.67 | $Sr(OAc)_2$ 8.22 | |
| 5 | 29.6 | AcOH 24.0 | Ni powder 0.208 | $CH_3I$ 13.9 | $Sn(OAc)_2$ 0.42 | $Si(OCH_3)_4$ 1.10 | LiOAc 2.64 |
| 6 | 29.6 | | $Ni(OAc)_2$ 0.625 | $CH_3I$ 13.9 | $Sn(OAc)_2$ 3.34 | LiOAc 2.64 | |
| 7 | 29.6 | AcOH 24.0 | $NiI_2$ 1.11 | $CH_3I$ 13.9 | $SnI_2$ 1.32 | $Cs(OAc)_2$ 6.32 | |
| 8 | 29.6 | AcOH 24.0 | $Ni(OAc)_2$ 1.25 | $CH_3I$ 13.9 | $Sn(OAc)_2$ 3.34 | LiOAc 3.96 | |
| 9 | 29.6 | AcOH 24.0 | $NiI_2$ 1.11 | $CH_2I$ 13.9 | $SiI_4$ 3.88 | LiOAc 2.64 | |
| 10 | 29.6 | AcOH 24.0 | $NiI_2$ 1.11 | | $SnI_2$ 2.64 | LiI 16.7 | |
| 11 | 29.6 | AcOH 24.0 | Ni powder 0.208 | $CH_3I$ 14.2 | $Sn(OAc)_2$ 0.42 | $GeI_4$ 4.1 | LiOAc 1.32 |
| 12 | 29.6 | AcOH 24.0 | Ni powder 0.29 | $I_2$ 13 | $SnI_2$ 1.32 | LiOAc 1.32 | 2.64 |

| Ex. No. | Reaction conditions Temperature (°C.) | Total pressure (atm.) | Partial pressure of $CO(H_2)$ (atm.) | Time (min) | Yield of acetic anhydride (%) | Formation Rate of Acetic Anhydride ( Acetic Anhydride (g) formed / [Ni;g] [I;g] [Hr] ) |
|---|---|---|---|---|---|---|
| 1 | 180 | 80 | 55(10) | 60 | 73.6 | 11.6 |
| 2 | 190 | 60 | 40(5) | 60 | 68.0 | 9.4 |
| 3 | 185 | 70 | 45(10) | 60 | 69.0 | 12.9 |
| 4 | 180 | 80 | 57(10) | 120 | 83.1 | 6.1 |
| 5 | 180 | 80 | 55(10) | 120 | 78.3 | 6.2 |
| 6 | 180 | 80 | 50(10) | 90 | 71.2 | 7.5 |
| 7 | 185 | 80 | 54(10) | 90 | 67.2 | 6.4 |
| 8 | 180 | 80 | 65 | 30 | 57.0 | 18.1 |
| 9 | 195 | 100 | 80(5) | 150 | 65.1 | 3.0 |
| 10 | 175 | 80 | 58(10) | 60 | 68.7 | 7.6 |
| 11 | 195 | 80 | 55(10) | 120 | 67.2 | 4.0 |
| 12 | 185 | 80 | 44(20) | 60 | 52.5 | 5.3 | formation rate of acetic anhydride =

$$\frac{\text{acetic anhydride (g) formed}}{[\text{nickel (g) used}] \times [\text{iodine (g) used}] \times [\text{hour}]}$$

EXAMPLE 1

A tantalum autoclave was charged with 29.6 g of methyl acetate, 24.0 g of acetic acid, 0.208 g of nickel powder, 13.9 g of methyl iodide, 1.67 g of stannous acetate and 2.64 g of lithium acetate. After the temperature had been raised to 180° C., carbon monoxide and hydrogen was fed under pressure to a pressure of 80 atm. (the partial pressure of carbon monoxide: about 55 atm., the partial pressure of hydrogen: about 10 atm.). Then, the reaction of methyl acetate and carbon monoxide

EXAMPLE 13

A tantalum autoclave was charged with 29.6 g of methyl acetate, 6.4 g of methanol, 12.0 g of acetic acid, 0.208 g of nickel powder, 13.9 g methyl iodide, 1.67 g of stannous acetate and 2.64 g of lithium acetate. After the temperature had been raised to 185° C., carbon monoxide and hydrogen was fed under pressure to a pressure of 80 atm. (the partial pressure of carbon monoxide: about 55 atm., the partial pressure of hydrogen: about 10 atm.) Then, the reaction was carried out at 185° C. for 1.3 hours while maintaining the pressure at 80 atm. by continuously feeding carbon monoxide into the autoclave. After completing the reaction, analysis showed that the yield of acetic anhydride was 71.1% on the basis of methyl acetate and the yield of acetic acid was approximately 100% on the basis of methanol. The formation rate of acetic anhydride was 8.6 [g]/[Ni;g]·[I;g][Hr].

EXAMPLE 14

A tantalum autoclave was charged with 24.0 g of acetic acid, 0.208 g of nickel power, 18.9 g of methyl iodide, 2.2 g of stannic iodide and 2.64 g of lithium acetate. After the temperature had been raised to 180° C., carbon monoxide was fed into the autoclave under pressure to a pressure of 60 atm. (the partial pressure of carbon monoxide: about 45 atm.) and the content was stirred. After 30 minutes of the stirring, 14.8 g of dimethyl ether was fed into the autoclave under pressure, and carbon monoxide and hydrogen were fed to establish a total pressure of 80 atm. Then, the reaction of dimethyl ether and carbon monoxide was carried out at 180° C. for 2.5 hours while maintaining the pressure at 80 atm. by continuously feeding carbon monoxide into the autoclave. After completing the reaction, analysis showed that the yield of acetic anhydride was 67.1% on the basis of dimethyl ether. The formation rate of acetic anhydride was 2.5 [g]/[Ni;g][I;g][Hr].

EXAMPLE 15

A tantalum autoclave was charged with 29.6 g of methyl acetate, 24.0 g of acetic acid, 0.208 g of nickel powder, 13.9 g of methyl iodide, 1.67 g of stannous acetate, 2.64 g of lithium acetate and 1.85 g of zirconyl acetate, $ZrO(OAc)_2$. After the temperature had been raised to 180° C., carbon monoxide and hydrogen was fed thereto under pressure to a pressure of 80 atm. (the partial pressure of carbon monoxide: about 60 atm., the partial pressure of hydrogen: about 5 atm.) Then, the reaction of methyl acetate and carbon monoxide was carried out at 180° C. for 45 minutes while maintaining the pressure at 80 atm. by continuously feeding carbon monoxide into the autoclave. After completing the reaction, analysis showed that the yield of acetic anhydride was 69.7% on the basis of methyl acetate.

EXAMPLES 16-21

Procedures similar to those of Example 14 were followed in which the feeding materials and reaction conditions shown in Table 2 were used.

The results obtained are given in Table 2 together with those of Example 14 and the control in which the catalyst system consisted essentially of 0.58 g of nickel powder, 18.0 g of methyl iodide and 5.1 g of tri-n-butyl amine. On analysis for the control, it was found that butyl acetate, methyl valerate and butyl iodide were formed in a total amount of 6%.

TABLE 2

| Ex. No. | AcOMe (g) | Solvent (g) | Nickel Component (g) | Halide (g) | Co-catalyst I (g) | Co-catalyst II (g) | Co-catalyst III (g) |
|---|---|---|---|---|---|---|---|
| 15 | 29.6 | AcOH 24.0 | Ni powder 0.208 | $CH_3I$ 13.9 | $Sn(OAc)_2$ 1.67 | LiOAc 2.64 | $ZrO(Ac)_2$ 1.85 |
| 16 | 29.6 | AcOH 24.0 | Ni powder 0.208 | $CH_3I$ 13.9 | $SnI_4$ 2.2 | LiOAc 2.64 | $ZrCl_4$ 1.92 |
| 17 | 29.6 | AcOH 24.0 | $Ni(OAc)_2$ 0.625 | $CH_3I$ 6.0 | $Sn(OAc)_2$ 0.84 | LiI 5.36 | $ZrOI_2$·4.15 |
| 18 | 29.6 | $Ac_2O$ 24.0 | $NiI_2$ 1.11 | $CH_3I$ 13.9 | $Sn(OAc)_2$ 1.67 | $Sr(OAc)_2$ 8.22 | $ZrOCl_2$·2.65 |
| 19 | 29.6 | | $Ni(OAc)_2$ 0.625 | $CH_3I$ 13.9 | $Sn(OAc)_2$ 3.34 | LiOAc 2.64 | $ZrOI_2$·8.30 |
| 20 | 29.6 | AcOH 24.0 | $NiI_2$ 1.11 | $CH_3I$ 13.9 | $SnI_2$ 1.32 | $Ca(OAc)_2$ 6.32 | $ZrOCl_2$·2.65 |
| 21 | 29.6 | AcOH 24.0 | Ni powder 0.208 | $CH_3I$ 14.2 | $Sn(OAc)_2$ 0.42 $GeI_4$ 4.1 | LiOAc 1.32 | $ZrOI_2$·$8H_2O$ 4.15 |
| Control | 29.6 | AcOH 24.0 | Ni powder 0.58 | $CH_3I$ 18.0 | Organic nitrogen group compound $(n-C_4H_9)_3N$ 5.1 | | |

| Ex. No. | Reaction conditions Temperature (°C.) | Total pressure (atm.) | Partial pressure of $CO(H_2)$ (atm.) | Time (min) | Yield of acetic anhydride (%) | Formation Rate of Acetic Anhydride $\left(\frac{\text{Acetic Anhydride (g) formed}}{[Ni;g]\ [I;g]\ [Hr]}\right)$ |
|---|---|---|---|---|---|---|
| 15 | 180 | 80 | 60(5) | 45 | 69.7 | 14.7 |
| 16 | 190 | 60 | 40(5) | 45 | 66.0 | 12.1 |
| 17 | 185 | 70 | 45(10) | 45 | 70.1 | 17.5 |
| 18 | 180 | 80 | 57(10) | 90 | 79.1 | 7.5 |
| 19 | 180 | 80 | 50(10) | 60 | 68.1 | 10.8 |
| 20 | 185 | 80 | 54(10) | 60 | 65.3 | 9.3 |
| 21 | 195 | 80 | 55(10) | 90 | 65.1 | 4.6 |
| Control | 200 | 100 | 75(5) | 6 hr. | 65.8 | 0.457 |

EXAMPLE 22

Into an autoclave equipped with liquid-withdrawing means were charged 44 g of acetic acid, 78 g of acetic anhydride, 72 g of methyl acetate, 47 g of methyl iodide, 1.7 g of nickel acetate, 4.7 g of tin acetate and 5.0 g of lithium acetate. The reaction was started at 180° C. and 80 $Kg/cm^2$·G (the partial pressure of CO was 58 $Kg/cm^2$ and the partial pressure of $H_2$ was 10 $Kg/cm^2$). The starting material, the solvent, the nickel catalyst, the halide and the co-catalyst were continuously fed into the autoclave and the reaction mixture was continuously withdrawn so that conversion of methyl acetate to acetic anhydride was maintained at 30%. The resulting acetic anhydride was continuously separated from the unreacted starting material, the catalyst, the solvent, the halide and the co-catalyst by distillation. The components other than acetic anhydride withdrawn from the autoclave were circulated into the autoclave. The reaction was continued for 12 hours. Methyl acetate was fed at a rate of 103 g/hr during the reaction. As a result acetic anhydride was formed at an average rate of 140 g/hr. During the reaction, acetic acid was formed as a by-product, but other by-products other than acetic acid were not detected.

EXAMPLES 23 AND 24

Procedures similar to those of Example 14 were followed. The feeding materials and reaction conditions, and the results obtained are given in Table 3.

TABLE 3

| Ex. No. | $CH_3OCH_3$ (g) | Solvent (g) | Nickel Component (g) | Halide (g) | Co-catalyst I (g) | Co-catalyst II (g) |
|---|---|---|---|---|---|---|
| 23 | 14.8 | AcOH 24.0 | $NiI_2$ 1.11 | $CH_3I$ 13.9 | $SnI_4$ 2.2 | LiI 5.36 |
| 24 | 14.8 | AcOH 24.0 | $Ni(OAc)_2$ 0.625 | $CH_3I$ 13.9 | $Sn(OAc)_2$ 1.67 | LiOAc 2.64 |

| Ex. No. | Reaction conditions Temperature (°C.) | Total pressure (atm.) | Partial pressure of $CO(H_2)$ (atm.) | Time (min) | Yield of acetic anhydride (%) | Formation Rate of Acetic Anhydride (g) $\left( \frac{\text{Acetic Anhydride (g) formed}}{[Ni;g][I;g][Hr]} \right)$ |
|---|---|---|---|---|---|---|
| 23 | 190 | 80 | 45(15) | 120 | 68.2 | 2.79 |
| 24 | 185 | 90 | 67(5) | 150 | 69.2 | 3.51 |

What is claimed is:

1. A process for producing acetic anhydride which comprises reacting methyl acetate or dimethyl ether with carbon monoxide at a temperature ranging from 80° to 300° C. and at a partial carbon monoxide pressure ranging from 0.5 to 300 atm. in the presence of a catalyst comprising (a) nickel or a nickel compound and (b) at least one halide selected from the group consisting of bromides, iodides and mixtures thereof, said nickel component being employed in an amount ranging from $1 \times 10^{-4}$ to 2 g-atom per liter of the reaction solution in terms of metallic nickel and said halide component being employed in an amount ranging from $1 \times 10^{-3}$ to 15 mol per liter of the reaction solution in terms of halogen atom, together with a co-catalyst comprising a Group IVB metal component and a Group IA metal and/or Group IIA metal component, said Group IVB metal component being one or more materials selected from the group consisting of silicon, germanium and tin belonging to Group IVB of the Periodic Table, compounds of these metals and mixtures thereof, said Group IA metal component being one or more materials selected from the group consisting of lithium, rubidium and cesium belonging to Group IA of the Periodic Table, compounds of these metals and mixtures thereof, and said Group IIA metal component being one or more materials selected from the group consisting of magnesium, calcium, strontium and barium belonging to Group IIA of the Periodic Table, compounds of these metals and mixtures thereof, each of said metal co-catalyst components being employed in an amount ranging from $1 \times 10^{-5}$ to 30 g-atom per liter of the reaction solution in terms of elementary metal.

2. The process as defined in claim 1 wherein said metal of Group IVB is tin.

3. The process as defined in claim 1 wherein said metal of Group IA is lithium.

4. The process as defined in claim 1 wherein said metal of Group IIA is selected from the group consisting of calcium and strontium.

5. The process as defined in claim 1 wherein said co-catalyst is a combination of (i) at least one material selected from the group consisting of silicon, germanium and tin belonging to Group IVB of the Periodic Table, compounds of the metals and mixtures thereof and (ii) at least one material selected from the group consisting of lithium, rubidium and cesium belonging to the Group IA of the Periodic Table, compounds of the metals and mixtures thereof.

6. The process as defined in claim 1 wherein said co-catalyst further contains one or more materials selected from the group consisting of metals belonging to Group IVA of the Periodic Table, compounds of the metals and mixtures thereof as a Group IVA metal co-catalyst component.

7. The process as defined in claim 6 wherein said metal of Group IVA is zirconium.

8. The process as defined in claim 1 wherein the amount of said nickel component is in the range of from $1 \times 10^{-3}$ to 1 g-atom per liter of the reaction solution in terms of metallic nickel.

9. The process as defined in claim 1 wherein the amount of said Group IVB metal component is in the range of 0.01 g-atom to 100 g-atom per 1 g-atom of nickel in terms of metal.

10. The process as defined in claim 1 wherein the amount of each of said Group IA metal and Group IIA metal components is in the range of 0.01 g-atom to 100 g-atom per 1 g-atom of nickel in terms of metal.

11. The process as defined in claim 6 wherein said Group IVA metal co-catalyst component is employed in an amount ranging from 0.01 g-atom to 100 g-atom per 1 g-atom of nickel in terms of metal.

12. The process as defined in claim 1 wherein said reaction temperature is between 100° C. and 250° C.

13. The process as defined in claim 1 wherein said partial pressure of carbon monoxide is between 1 and 200 atm.

14. The process as defined in claim 8 wherein the amount of said nickel component is in the range of from $5 \times 10^{-3}$ to 0.5 g-atom per liter of the reaction solution in terms of metallic nickel.

15. The process as defined in claim 9 wherein the amount of said Group IVB metal component is in the range of from 0.03 to 30 g-atom per gram-atom of nickel in terms of elementary metal.

16. The process as defined in claim 9 wherein the amount of said Group IVB metal component is in the range of from 0.01 to 20 g-atom per gram-atom of nickel in terms of elementary metal.

17. The process as defined in claim 10 wherein the amount of each of said Group IA metal and Group IIA metal components is in the range of from 0.03 to 1 g-atom of nickel in terms of elementary metal.

18. The process as defined in claim 10 wherein the amount of each of said Group IA metal and Group IIA metal components is in the range of from 0.1 to 20 g-atom of nickel in terms of elementary metal.

19. The process as defined in claim 11 wherein the amount of said Group IVA metal co-catalyst component is in the range of from 0.03 to 30 g-atom per gram-atom of nickel in terms of elementary metal.

20. The process as defined in claim 11 wherein the amount of said Group IVA metal co-catalyst component is in the range of from 0.1 to 20 g-atom per gram-atom of nickel in terms of elementary metal.

21. The process as defined in claim 6 wherein the amount of said Group IVA metal co-catalyst component is in the range of from $10^{-5}$ to 30 g per liter of the reaction solution in terms of elementary metal.

22. The process as defined in claim 1 wherein the amount of said halide component is in the range of from $1 \times 10^{-2}$ to 8 mole per liter of the reaction solution in terms of halogen atoms.

23. The process as defined in claim 22 wherein the amount of said halide component is in the range of from $1 \times 10^{-1}$ to 4 mol per liter of the reaction solution in terms of halogen atoms.

24. The process as defined in claim 22 wherein the amount of said halide component is in the range of from $2 \times 10^{-1}$ to 2.5 mol per liter of the reaction solution in terms of halogen atoms.

* * * * *